United States Patent
De Man

(10) Patent No.: US 12,201,500 B2
(45) Date of Patent: Jan. 21, 2025

(54) TUBULAR BANDAGE

(71) Applicant: De Man Projects SA, Luxembourg (LU)

(72) Inventor: Cedric Lodewijk H. De Man, Bertrange (LU)

(73) Assignee: De Man Projects SA, Luxembourg (LU)

( * ) Notice: Subject to any disclaimer, the term of this patent is extended or adjusted under 35 U.S.C. 154(b) by 0 days.

(21) Appl. No.: 18/141,043

(22) Filed: Apr. 28, 2023

(65) Prior Publication Data

US 2024/0099895 A1    Mar. 28, 2024

Related U.S. Application Data

(63) Continuation of application No. 17/005,653, filed on Aug. 28, 2020, now abandoned, which is a
(Continued)

(30) Foreign Application Priority Data

Jun. 27, 2011    (BE) .................. 201100385

(51) Int. Cl.
  *A61F 13/01*    (2024.01)
  *A61F 13/00*    (2024.01)
  (Continued)

(52) U.S. Cl.
  CPC .. *A61F 13/01038* (2024.01); *A61F 13/00987* (2013.01); *A61F 13/01029* (2024.01);
  (Continued)

(58) Field of Classification Search
  CPC .... A61F 13/00–0293; A61F 13/06–069; A61F 13/10–108; A61F 5/01–0109;
  (Continued)

(56) References Cited

U.S. PATENT DOCUMENTS 2,858,830 A    11/1958    Robins
2,882,528 A    4/1959    Tassie
(Continued)

FOREIGN PATENT DOCUMENTS

FR    2213856 A1    8/1974
GB    191319869 A * 8/1914
NL    1020417 A1    10/2003

OTHER PUBLICATIONS

Fabrifoam Universal Wrist Wrap, 2024, North Coast Medical Rehabilitation Products, https://www.ncmedical.com/products/fabrifoam-universal-wrist-wrap_1210.html (Year: 2024).*
(Continued)

*Primary Examiner* — Michelle J Lee
(74) *Attorney, Agent, or Firm* — Dinsmore & Shohl LLP

(57) ABSTRACT

Tubular bandage, in particular a finger or toe bandage which is formed as a tube comprising an outer layer which is connected to an inner layer, and wherein the outer layer has a diameter and an elasticity such that the bandage can be clamped adhesive-free around the body part to be treated, in the particular, said finger or said toe, and wherein the inner layer is made of an elastic wound-protective material, wherein said outer layer is made of an air-permeable and water-repellent material, and wherein, at the open endings, said outer layer extends in the longitudinal direction over the inner layer over a distance of more than 0.5 mm, such that the outer layer touches the body part to be treated, in particular a finger or toe, with its endings when applied.

4 Claims, 2 Drawing Sheets

Related U.S. Application Data continuation of application No. 14/128,735, filed as application No. PCT/IB2012/053232 on Jun. 26, 2012, now abandoned.

(51) Int. Cl.
*A61F 13/06* (2006.01)
*A61F 13/10* (2006.01)

(52) U.S. Cl.
CPC .......... *A61F 13/068* (2013.01); *A61F 13/105* (2013.01); *A61F 2013/00093* (2013.01); *A61F 2013/00119* (2013.01); *A61F 2013/00217* (2013.01); *A61F 2013/0048* (2013.01); *Y10T 156/10* (2015.01)

(58) Field of Classification Search
CPC ..................... A61F 5/013; A61B 17/12; A61B 17/132–1355; Y10T 156/10; B29C 66/522; B29C 66/5221; B29C 66/5227–52272; B29C 66/53–53241; B29C 66/53245
See application file for complete search history.

(56) References Cited

U.S. PATENT DOCUMENTS

| | | | |
|---|---|---|---|
| 3,972,328 A | 8/1976 | Cheng | |
| 4,324,246 A * | 4/1982 | Mullane | A61F 13/512 604/371 |
| 4,530,353 A | 7/1985 | Lauritzen | |
| 4,828,556 A | 5/1989 | Braun et al. | |
| 5,059,424 A | 10/1991 | Cartmell et al. | |
| 5,181,914 A | 1/1993 | Zook | |
| 6,011,194 A * | 1/2000 | Buglino | B32B 5/22 428/326 |
| 6,139,514 A | 10/2000 | Benson | |
| 6,605,172 B1 * | 8/2003 | Anderson | B32B 27/12 156/199 |
| 7,012,169 B2 | 3/2006 | McDevitt et al. | |
| 2002/0095107 A1 | 7/2002 | Martin | |
| 2003/0108633 A1 | 6/2003 | Yamakawa et al. | |
| 2005/0033212 A1 | 2/2005 | Scheinberg et al. | |
| 2008/0262403 A1 | 10/2008 | Martin | |
| 2010/0100025 A1* | 4/2010 | Kane | A61B 17/1322 606/203 |
| 2013/0110026 A1 | 5/2013 | Jackson et al. | |

OTHER PUBLICATIONS

International Search Report for International Application No. PCT/IB2012/053232 dated May 13, 2013.
International preliminary Report on Patentability for International Application No. PCT/IB2012/053232 dated Jan. 7, 2014.

* cited by examiner

TUBULAR BANDAGE

CROSS-REFERENCES TO RELATED APPLICATIONS

This application is a continuation of U.S. patent application Ser. No. 14/128,735, filed Dec. 23, 2013, which is a national-phase application under 35 U.S.C. § 371 of International Application PCT/IB2012/053232, filed Jun. 26, 2012, which International Application claims benefit of priority to Belgian Patent Application 201100385, filed Jun. 27, 2011.

BACKGROUND

The invention relates to a tubular bandage, and in particular a finger or toe bandage, which is formed as a tube extending along a longitudinal axis and which is open at two endings, wherein said tube comprises an outer layer and an inner layer, wherein the outer layer is connected to an inner layer, and wherein the outer layer has a diameter and an elasticity such that the bandage can be clamped adhesive-free around the body part to be treated, in particular, said finger or said toe, and wherein the inner layer is made of an elastic wound-protective material, and wherein said outer layer is made of an air-permeable and water-repellent material. As is apparent from the following description, the bandage of the present invention is characterized by the fact that, near the open endings, said outer layer extends over the inner layer over a distance of more than 0.5 mm, such that the outer layer touches the body part to be treated with its endings, in particular, the finger or toe, when applied.

People performing manual labour in a wet and/or dirty environment, such as cooks, electricians, builders, carpenters, barbers, and the like, often contract wounds to the fingers, for example through impact or cutting. These wounds are usually not of such a nature that they impede the completion of their work. However, the wound should not come into contact with the wet and/or dirty environment, as complications in the healing process of the wound may occur. A tubular finger or toe bandage which can be applied adhesive-free around a finger or toe, is particularly suitable for the treatment of such wounds. Such a bandage can be applied as a more or less broad ring around the finger at the location of the wound, allowing the bandage to close off the wound from the environment. As the bandage is clamping around the finger as a ring, an adhesive layer is not necessary, and hence, an adhesive layer cannot become detached from the finger. Therefore, the tubular bandage will remain better in place where it was applied rather than a conventional planar bandage with adhesive strips, also during subsequent manual labour.

Such a tubular bandage is for example known from U.S. Pat. No. 2,882,528 (Tassie, 1957). This bandage has a shape, in particular the shape of the outer layer, which makes this bandage complex and therefore expensive to manufacture. This bandage does not comprise an outer layer of which the endings extends over the inner layer, and thereby closing off the inner layer from the environment by clamping.

Furthermore, such a bandage is known from US 2002/0095107 (Martin, 2002). This patent publication describes a bandage for a finger or toe, which is formed as a tube (see FIG. 8 of said publication), and which comprises an inner layer and an outer layer (see FIG. 6 of said publication). The outer layer is made of a material having a diameter and elasticity such that the bandage can be clamped around a finger or toe. Furthermore, the production process for manufacturing such a bandage is optimized by manufacturing the bandage as a continuous band, as shown in cross-section in FIG. 7 of said publication, and subsequently by cutting it into segments (see paragraph [0066] in the latter publication). As a result, this bandage does not comprise an outer layer of which the endings extend over the inner layer, thereby closing off the inner layer from the environment by clamping.

Furthermore, such a bandage is known from U.S. Pat. No. 6,139,514 (Benson, 2000). This patent publication describes a bandage for a finger which is formed as a sleeve with one open ending and one closed ending (see FIG. 1 of said publication), and comprising an inner layer and an outer layer. The outer layer is made of a material having a diameter and elasticity such that the bandage can be clamped around a finger. This bandage comprises an outer layer of which the endings extend over the inner layer, but which is further provided with an adhesive layer to hold the bandage into place.

Furthermore, such a bandage is known from US 2008/0262403 (Martin, 2008). This patent publication describes a bandage, for example, for a finger, which is formed as a tube with two open endings (see FIG. 5 of said publication), and comprising an inner layer made of an elastic fabric and an outer layer. The outer layer is made of a material having a diameter and elasticity such that the bandage can be clamped around a finger or toe. Furthermore, the production process for the manufacture of such a bandage is optimized by manufacturing the bandage as a continuous band, as shown in cross-section in FIG. 5 of said publication, and subsequently by cutting it into segments (see paragraph [0051] in the latter publication). As a result, this bandage does not comprise an outer layer of which the endings extend over the inner layer, thereby closing off the inner layer from the environment by clamping. Because the outer layer comprises a textile, the edge of this bandage is also prone to fraying, which is undesirable.

The bandages of the prior art have the drawback that they are not suitable for use in dirty and/or wet environments. In such environments, the bandage will allow dirt and/or moisture to penetrate the bandage such that the bandage loses its protective function. A further problem is that the bandage does not prevent wound fluids from exiting the bandage. It will be obvious that it is unacceptable, for example in the food sector, to use bandages that do not contain wound fluids within the bandage, as it would cause food to get contaminated with wound fluids.

SUMMARY

The invention aims to provide a bandage, which, in a dirty and/or wet environment, also has a protective function when applied over a finger or toe. To the extent that, in the present invention, reference is made to a finger or toe bandage, it is obvious that, depending on the selected diameter, the tubular bandage as described herein, can also be used for the treatment of wounds at all kinds of substantially cylindrical parts of the body, in particular, a leg, arm, finger, toe, wrist, or even a leg in veterinary applications. Furthermore, the tubular bandage may also have a profile that varies along its length such that the tubular bandage has an even better fit around the body part, while following the contours thereof, such as, for example, an ankle or an upper arm. Hence, the invention also aims to provide a tubular bandage which comprises a radial outer layer which is connected to a radial inner layer, and wherein the outer layer has a diameter and an elasticity such that the bandage can be clamped adhesive-free around the body part to be treated, and wherein the inner layer is made of an elastic wound-protective material, characterized in that said outer layer is made of an air-permeable and water-repellent material, and in that, at every point at the open endings, said outer layer extends in the longitudinal direction over the inner layer over a distance of more than 0.5 mm, such that by the combination of distance, diameter and elasticity of the outer layer, the latter touches the body part to be treated with its endings when applied, in order to close off the inner layer of the environment.

Hence, the diameter of the radial outer layer of the tubular bandage is dependent on the body part to be treated and should be of such a nature that the bandage can be clamped adhesive-free around the body part to be treated. For example, when using it as a finger or toe bandage, the diameter will be in a range of about 1.5 cm up to about 3.0 cm; when using it as a leg bandage, the diameter will be in the typical range of about 10.0 cm up to about 20.0 cm; when using it as a arm bandage, the diameter may be in a typical range of about 5.0 up to about 15.0 cm.

The invention further aims to provide a bandage wherein wound fluid is contained within the bandage when applied over a body part, in particular a finger or toe.

The invention further aims to provide a bandage which can easily be manufactured, and which has an edge or rim that is not fraying.

To this end, the bandage according to the invention is characterized in that said outer layer is made of an air-permeable and water-repellent material, and in that, at every point at the open endings, said outer layer extends in the longitudinal direction over the inner layer over a distance of more than 0.5 mm, such that by the combination of distance, diameter and elasticity of the outer layer, the latter touches the finger or toe with its endings when applied, in order to close off the inner layer of the environment. When the bandage is applied over the finger or toe, the outer layer of the tube touches the finger at both open endings, as the edge of the outer layer extends over the inner layer, such that the inner layer is closed off from the environment. The outer layer is made of a water-repellent but air-permeable material, such that dirt nor moisture can penetrate the outer layer, yet the wound is not air-tight sealed off from the environment. By this combination, the inner layer is completely closed off from a dirty and/or wet environment, such that the bandage maintains its protective function, even under difficult circumstances. Furthermore, such a bandage will enclose the wound such that, under normal conditions, no wound fluid will leave the bandage. By this specific shape, an outer edge is created on the bandage which ensures that the wound is sealed off from the environment.

In particular, that part of said outer layer of which the endings extend in the longitudinal direction over the inner layer, thereby closing off the inner layer from the environment, in particular the outer edge, does not comprise an adhesive.

Preferably, said distance is more than 1 mm, preferably about 2, 3, 4, 5, 6, 7, 8, 9, or 10 mm; in particular about 2 mm. When a bandage is applied over a body part to be treated, such as a finger or toe, to protect a wound on said finger or toe, the finger or toe can be subsequently used again. The body part, such as for example, the finger or toe, will in practice, after application of the bandage, be able to move, and preferably, the bandage is formed such that a movement does not result in the fact that the outer layer no longer touches the body part, such as for example, the finger or toe, at the open endings. For this would result in dirt and/or moisture from the environment coming into contact with the wound, causing the bandage to lose its function. By selecting a distance of more than 1 mm, preferably about 2, 3, 4, 5, 6, 7, 8, 9, or 10 mm, and in particular about 2 mm, the ability of the outer layer to follow the movement of the body part to be treated, and in particular, the finger or toe, and thus to keep the open endings closed off, is considerably increased such that a bandage with a greater protective ability is obtained. In other words, the outer edge closing off the wound from the environment, will be larger.

Of course, and by analogy with the diameter, the length of the tubular bandage according to present invention will be determined by the body part to be treated. For example, in the treatment of a leg, arm, or even a leg in veterinary applications, the length of the tubular bandage, i.e. the length of the inner layer, will typically be in a range of about 5.0 cm to about 30.0 cm. In the application to small body parts, such as a finger or toe, said tube has a length which is less than 30 mm, preferably less than 25 mm, more preferably less than 20 mm. The length of the bandage determines the covering ability of the bandage, and thus determines the suitability of the bandage to treat a wound with a given size. The bandage according to the invention will be particularly suited for the treatment of relatively small wounds. If the wound is so large that it extends over the entire finger or toe, bandages from the state of the art, which are intended to cover the entire finger or toe, will be preferred. However, if the wound is rather small, for example a local cutting or abrasion wound, such a bandage from the state of the art, covering the entire finger or toe, is no longer preferred, since said bandage will substantially reduce mobility and pressure sensitivity of the finger or toe, such that the normal functions of the finger or toe are substantially limited. Hence, in the specific use of the bandage according to the invention as a toe or finger bandage, preferably this bandage has a length which is less than 3 centimetres, preferably less than 2 centimetres, and more preferably less than 1.5 centimetres, and by this length is provided to minimally interfere with the normal functions of the finger or toe and yet to tightly cover the wound.

Preferably, said outer layer is made of a thermoplastic elastomer. Thermoplastic elastomers (TPE's) are known for their good elasticity. In particular, TPE elastomers with a hardness of 25 Shore A to 80 Shore A are especially suitable for use in the invention. An outer rim made of such a thermoplastic elastomer does not fray, not even with heavy or prolonged use.

Preferably, said inner layer is made as a compress and/or a hydrocolloid substance. The use of a compress and/or hydrocolloid substance as a wound-protective material or as a part thereof, has a stimulating effect on the healing process of the wound. A compress is a sterile gauze that is optionally wet, and that is arranged such that it fits tightly onto the wound. By the combination of a sterile gauze and the tension exerted by clamping, bleeding of the wound is prevented. A hydrocolloid substance is a visco-elastic gel-like material that is used to cover wounds, and that is known to have a good wound healing ability.

Preferably, said inner layer has a substantial elasticity in both the longitudinal and transversal direction. Such an elasticity of the inner layer facilitates the application of the bandage according to the invention. Preferably, the inner layer has an elasticity which is more than the elasticity of the outer layer, such that the inner layer is not detached from the outer when applying the bandage.

The invention further relates to a method for the manufacture of a tubular bandage according to any one of the above-mentioned embodiments, and in particular a finger or toe bandage, wherein the method comprises the steps of:

manufacturing a tubular outer layer with two open endings;

sliding the outer layer thus manufactured over a rotatable shaft;

rotating the rotatable shaft provided with the outer layer;

moving from the outward in radial direction towards the rotating axis an inner layer applicator to apply an inner layer to the outer layer, wherein the inner layer applicator is provided to stay clear from the endings of the outer layer for at least 0.5 mm in the longitudinal direction.

According to this method, bandages according to the invention can easily and economically be manufactured. The bandages are manufactured and packaged inside-out, and will be turned inside-out when applied by a user, to direct the wound-protective material to the inside of the tubular bandage.

The invention will now be further described with reference to an exemplary embodiment shown in the drawing.

BRIEF DESCRIPTION OF THE DRAWINGS

In the drawing.

In the drawing, to the same or an analogous element is assigned the same reference numeral.

DETAILED DESCRIPTION

The figures show a finger or toe bandage 1. This finger or toe bandage has an outer layer 2 having the form of a tube which is open at its two distal endings. The outer layer is manufactured preferably tubular, in one piece and non-interrupted. This outer layer is made of an elastic material such as a rubber or a latex, or a thermoplastic elastomer. This outer layer further has a diameter D which is chosen such that the bandage without adhesive can be clamped around a finger or toe. The diameter is preferably between 0.5 cm and 3 cm, measured when the bandage is in its unstretched state, and measured on the inside of the outer layer. More preferably, the diameter is between 1 cm and 2 cm.

The outer layer 2 is made air-permeable. This allows the healing process to be promoted. A TPE outer layer can be made air-permeable by providing small openings or holes through the outer layer. The outer layer may be punctured in order to create such openings. Furthermore, the outer layer 2 is made water-repellent. This allows to avoid the penetration of dirt into the wound. Preferably, the bandage is made of an hypo-allergenic material. An example of a material that is suitable for manufacturing the outer layer, is a thermoplastic elastomer (TPE), Shore A, 25 to 80. This material has an elasticity which is very suitable for the bandage according to the invention.

The finger or toe bandage has a width B which is chosen such that the bandage is able to cover a local wound on a finger or toe. The width B of the bandage is measured parallel to the longitudinal axis 3 of the finger or toe bandage, and from the one distal ending to the opposite distal ending. Preferably, the width B of the bandage is not more than 3 inches, more preferably not more than 2.5 centimetre. For bandages with a smaller diameter, the width B of the bandage will preferably be not more than 2.0 centimetre.

The outer layer 2 is at least partially provided on an inside with an inner layer comprising at least a wound-protective material 4. The wound-protective material preferably comprises a compress and/or hydrocolloid substance. A compress can be defined as a gauze folded together several times, that is used in surgery as a bandage. The advantage of a gauze, in particular a compress, in the elastic finger or toe bandage according to the invention is that a gauze can stretch along with the elastic outer layer of the bandage. Preferably, the wound-protective material 4 is substantially stretchable in two different directions in the plane of the body of the bandage. The wound-protective material 4 can also be formed as a powder which is attached to the outer layer. The wound-protective material 4 is connected with the outer layer by traditional gluing or by ultrasonic bonding. The inner layer has a thickness between 0.4 mm and 2 mm.

Figure 1:
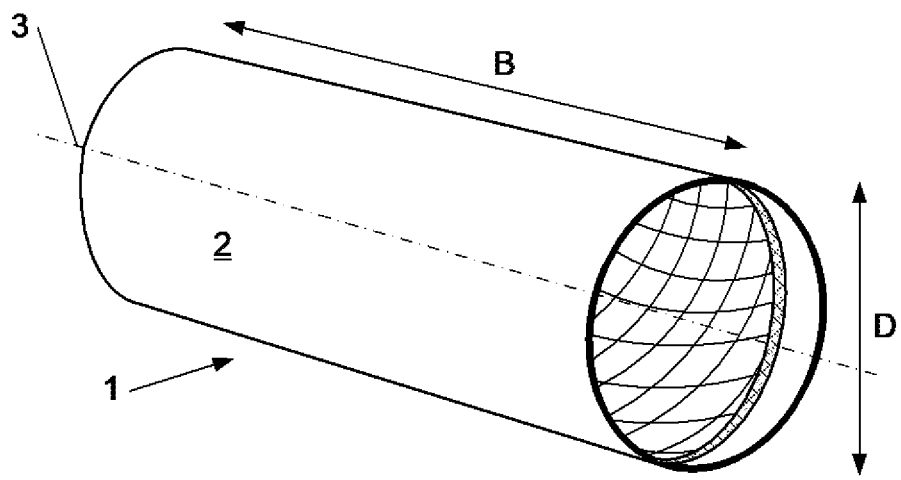
FIG. 1 shows a bandage according to the invention.
Figure 2:
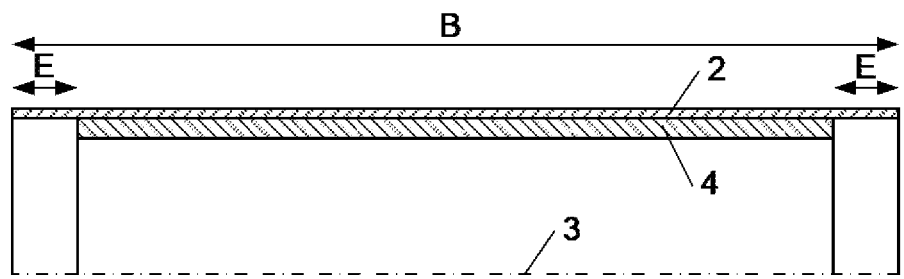
FIG. 2 shows a cross-section of a bandage according to the invention in a non-applied state.

FIG. 2 shows a cross-section of the finger or toe bandage, and shows in particular how the endings have been designed. At the distal endings, the outer layer 2 extends in the longitudinal direction over the inner layer 4 over a distance E. This distance E is at least more than 0.5 mm, preferably more than 1.0 mm, more preferably more than 1.5 mm, most preferably about 2 mm. The technical effect of this distance E is clearly shown in FIG. 3.

Figure 3:
FIG. 3 shows a cross-section of a bandage according to the invention in an applied state.

FIG. 3 shows a cross-section of the finger or toe bandage, wherein the latter is applied onto a finger or toe. As described above, the diameter and the elasticity of the outer layer of the bandage is such that the bandage clamps onto the finger or toe. By combining this technical feature with the distance E, as described above, the endings of the outer layer will bend towards the finger or toe, and touch the finger or toe, as is shown in FIG. 3. As a result, the inner layer 4 is closed off from the environment, and also the environment is closed off from the wound which is covered by the bandage.

Figure 4A:
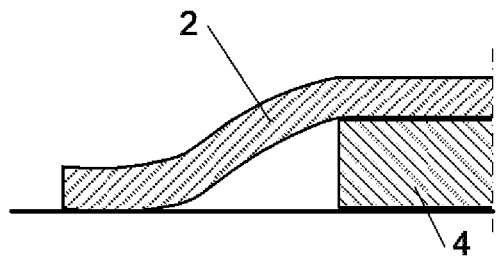
FIGS. 4A and 4B show a detail of the edge of the bandage according to the invention.
Figure 4B:
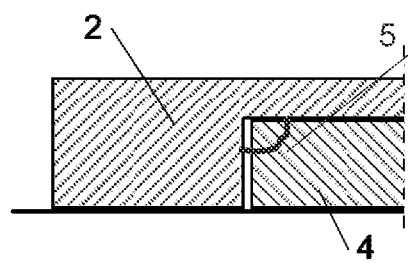

FIG. 4a shows in detail how the endings of the outer layer of the bandage, as a result of the elasticity, diameter and distance E, are adjoining the finger. FIG. 4b shows an alternative in which the clamping of the outer layer of the bandage, at its endings, against the finger is reinforced by the application of an edge 5 at its endings and on the inside of the outer layer. The edge may be formed by a thickening of the outer layer in the direction of the longitudinal axis 3 of the bandage.

As, following the construction of the bandage according to the invention, the outer layer completely encloses the inner layer such that the inner layer in use does not come into contact with the environment, the bandage according to the invention is very suitable for covering wounds. However, by the above-described functionality, the invention is equally very suitable for the application of medication as a transdermal bandage. For this purpose, the inner layer may comprise medication which is absorbed through the skin. An example of such a medication is nicotine, such that a nicotine bandage is obtained. Because the outer layer of the bandage completely closes off the inner layer from the environment, also the medication is closed off from the environment. This means that said medication is not able to contaminate the environment. Also, the medication, when the bandage is in a humid or aqueous environment, is not able to dissolve into said environment, as the inner layer is sealed off from the environment.

Figure 5:
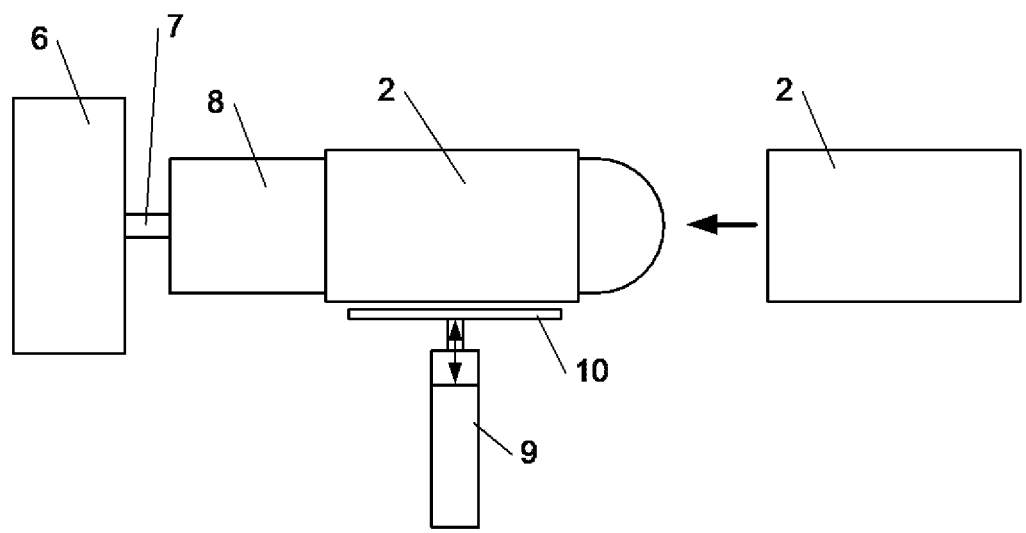
FIG. 5 show a device for the manufacture of a bandage according to the invention.

FIG. 5 shows a device for the manufacture of a bandage according to the invention. Said device comprises a motor 6 which drives a shaft 7, onto which shaft a bandage holder 8 is mounted. The shaft 7 is provided to have mounted bandage holders 8 with different diameters. The bandage holder is formed such that an outer layer 2 of a finger or toe bandage can be slid onto the bandage holder 8. Since outer layers 2 with different thicknesses are provided, also different associated bandage holders 8 should be provided. The device further comprises a piston 9 which is able to radially move an inner layer applicator 10 towards the bandage holder 8. The inner layer applicator 10 is provided to attach an inner layer 4 to the outer layer 2 provided over the bandage holder 8. The inner layer applicator 10 is further provided, when applying the inner layer, to stay clear at least 0.5 mm from the endings of the outer layer.

Figures 6, 7:
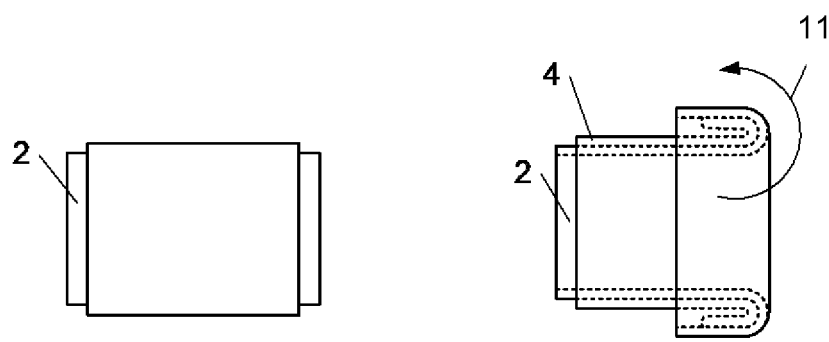
FIG. 6 shows a bandage which is manufactured by the method according to the invention.
FIG. 7 shows a bandage which is manufactured by the method according to the invention when turning it inside-out, and FIG. 8 show a variant of a bandage according to the invention, which is provided at one open side to clear a fingernail.

On the device as shown in FIG. 5, a bandage is formed as shown in FIG. 6. This bandage is technically constructed in the same way as the bandage shown in the FIGS. 1-4, however, inside-out. To use the bandage to cover a wound on a finger or toe, the bandage is turned inside-out in advance, or during the application according to the arrow 11 as shown in FIG. 7. It will therefore be appreciated that the finger or toe bandage in a state as shown in FIG. 6 will be within the scope of protection of the claims when said bandage is suitable to be turned inside-out as shown in FIG. 7.

Figure 8:
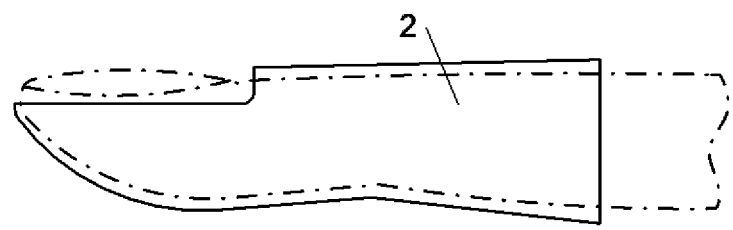

FIG. 8 shows a variant of a bandage according to the invention, in which the opening of the tube on one side is shaped such as to clear the finger nail, for example, to allow working with the nail. The edges around the preformed opening such that the fingernail is cleared, close off the inside of the bandage from the environment, as described above. The preformed opening may be adapted to the size of the finger or toe nail.

In embodiments, manufacturing of the bandage is done by first extruding a plastic tube and subsequently cutting off a segment of the tube, which segment forms said tubular outer layer. In other embodiments, before applying the inner layer, an adhesive is applied to the outer layer. In still other embodiments, after the bandage is manufactured, the bandage is packaged in a package, and the manufacturing is carried out under sterile conditions.

What is claimed is:

1. A method for manufacturing a tubular bandage, wherein:
   the tubular bandage extends along a longitudinal axis in a longitudinal direction;
   the tubular bandage comprises a tube that is open at two endings;
   the tube comprises a radial tubular outer layer that is connected to a radial inner layer;
   the outer layer has a diameter and an elasticity such that the bandage can be clamped adhesive-free around a body part to be treated;
   the inner layer is made of an elastic wound-protective material;
   the outer layer is made of an air-permeable and water-repellent material; and
   at every point at the open two endings, the outer layer extends in the longitudinal direction over the inner layer by a distance of more than 0.5 mm, such that by a combination of distance, diameter, and elasticity of the outer layer, the outer layer touches the body part to be treated with its endings when applied, to close off the inner layer from an environment;
   the method comprising:
   manufacturing the tubular outer layer with the two open endings;
   sliding the tubular outer layer thus manufactured over a rotatable shaft;
   rotating the rotatable shaft provided with the tubular outer layer; and
   moving an inner layer applicator in a radial direction toward a rotating axis of the rotatable shaft from outside the rotatable shaft to apply the inner layer to the outer layer, wherein the inner layer applicator is provided to stay clear from the two open endings of the outer layer for at least 0.5 mm in the longitudinal direction.

2. The method according to claim 1, wherein said manufacturing is done by first extruding a plastic tube and subsequently cutting off a segment of the tube, which segment forms said tubular outer layer.

3. The method according to claim 1, wherein, before applying the inner layer, an adhesive is applied to the outer layer.

4. The method according to claim 1, further comprising packaging the bandage in a package, and wherein the method is carried out under sterile conditions.

* * * * *